(12) United States Patent
Shimaoka

(10) Patent No.: US 6,469,786 B2
(45) Date of Patent: Oct. 22, 2002

(54) PARTICLE SIZE ANALYZER BASED ON THE LASER DIFFRACTION METHOD

(75) Inventor: Haruo Shimaoka, Nara (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/912,480

(22) Filed: Jul. 26, 2001

(65) Prior Publication Data
US 2002/0036776 A1 Mar. 28, 2002

(30) Foreign Application Priority Data
Aug. 4, 2000 (JP) ........................................ 2000-237492

(51) Int. Cl.$^7$ .............................................. G01N 15/02
(52) U.S. Cl. ...................... 356/336; 356/338; 356/343; 356/340
(58) Field of Search ................................ 356/338, 343, 356/336, 340

(56) References Cited

U.S. PATENT DOCUMENTS 5,185,641 A * 2/1993 Igushi et al. ................. 356/336
6,417,920 B1 * 7/2002 Shimaoka ..................... 356/336

* cited by examiner

Primary Examiner—Georgia Epps
Assistant Examiner—Tuyen Tra
(74) Attorney, Agent, or Firm—Kanesaka & Takeuchi

(57) ABSTRACT

Scattered light obtained by irradiating parallel laser beam to particles to be measured is condensed by a condenser lens in a wide angle area from 0° to over 40°, and an intensity distribution of the light is spatially continuously measured by an optical sensor positioned at a focal point of the condenser lens. Before a particle size distribution is calculated from the measured light intensity distribution, measuring error of the scattered light intensity distribution caused by an aberration by the condenser lens and an attenuation on the optical path is corrected by comparing with data obtained through a ray tracing in advance. Thus, the scattered light in a wider angle area are spatially continuously measured to thereby obtain a light intensity distribution with a high resolution in a submicron area.

4 Claims, 2 Drawing Sheets

PARTICLE SIZE ANALYZER BASED ON THE LASER DIFFRACTION METHOD

BACKGROUND OF THE INVENTION AND RELATED ART STATEMENT

The invention relates to a particle size analyzer based on the laser diffraction method, more specifically, a particle size analyzer based on the laser diffraction method wherein a particle size in a submicron area can be measured with a high resolution.

In a conventional particle size analyzer based on the laser diffraction method, generally, a spatial intensity distribution of scattered light generated by irradiating laser beam to particles to be measured in a dispersion state, is measured. Since the light intensity distribution conforms to a Mie's scattering theory or Fraunhofer's diffraction theory, a particle size distribution of the particles to be measured is calculated from the measured results of the spatial intensity distribution of the scattered light through a calculation based on the Mie's scattering theory or the Fraunhofer's diffraction theory.

In the conventional particle size analyzer of this type, as an optical system for measuring the spatial intensity of the scattered light by the particles to be measured, an apparatus shown in FIG. 2 (Japanese Patent No.2139485) has been widely used.

More specifically, laser beam as parallel beam is irradiated to a flow cell 21, in which a suspension S prepared by dispersing particles P to be measured in a medium liquid flows, by an irradiation optical system 22 formed of a laser beam source 22a, condenser lens 22b, spatial filter 22c and collimator lens 22d. The laser beam is scattered by the particles P to be measured in the suspension S to thereby produce a spatial light intensity distribution pattern. In the scattered light, light in a scattering angle smaller than 35° at the most in a predetermined forward angle are condensed by a condenser lens 23 to form a scattering image on a ring detector 24 positioned at a focal point of the lens. The ring detector 24 is structured such that several tens of light receiving elements, each having a light receiving surface with a ring shape, a semi-ring shape or a quarter ring shape, of different radii are coaxially arranged around an optical axis of the irradiation laser beam, so that the intensity of the scattered light condensed by the condenser lens 23 can be continuously measured in every small angle. Also, the light scattered forwardly in the large angle and laterally and rearwardly, which are not condensed by the condenser lens 23, are detected by forward large angle scattered light sensors 25, sideward scattered light sensors 26 and rearward scattered light sensors 27, formed of independent light sensors, respectively.

The spatial intensity distribution pattern of the scattered light measured as described above is digitized by an A–D converter; then taken into a computer as scattered light intensity distribution data; and converted into the particle size distribution of the particles P to be measured according to a theory explained below.

The intensity distribution data of the light scattered by the particles P to be measured vary according to the sizes of the particles. Since the actual particles P to be measured contain particles with different sizes, the intensity distribution data of the scattered light generated by the particles P to be measured become a superposition of the lights scattered from the respective particles. When this is expressed by a matrix, $$s = Aq \quad (1)$$

wherein, $$s = \begin{bmatrix} s_1 \\ s_2 \\ \vdots \\ s_m \end{bmatrix}, \quad q = \begin{bmatrix} q_1 \\ q_2 \\ \vdots \\ q_n \end{bmatrix} \quad (2)$$

$$A = \begin{bmatrix} a_{1 \cdot 1} & a_{1 \cdot 2} & \cdots & a_{1 \cdot n} \\ a_{2 \cdot 1} & \cdots & & \\ \vdots & & a_{i \cdot j} & \vdots \\ a_{m \cdot 1} & & \cdots & a_{m \cdot n} \end{bmatrix} \quad (3)$$

In the above respective formulas, s (vector) is intensity distribution data (vector) of the scattered light. Elements $s_i$ (i=1, 2, ... m) are incident light quantities detected by the respective elements of the ring detector 24 and the forward large angle, sideward and rearward scattered light sensors 25, 26, 27.

q (vector) is particle size distribution data (vector) expressed as a frequency distribution percentage. A diameter range of the particles to be measured (largest particle diameter: $X_1$, the smallest particle diameter: $X_{n+1}$) is divided into n, and an interval between the respective particle diameters is expressed by $[X_j, X_{j+1}]$ (j=1, 2, ... n). The elements $q_j$ (j=1, 2, ... n) of q (vector) are particle quantities corresponding to the particle diameter intervals $[X_j, X_{j+1}]$.

Generally, a normalization is carried out to obtain $$\sum_{j=1}^{n} q_j = 100\% \quad (4)$$

A (matrix) is a coefficient matrix for converting the particle distribution data (vector) q to the light intensity distribution data (vector) s. The physical meaning of elements ai, (i=1, 2, ... m, j=1, 2, ... n) of A (matrix) is an incident light quantity with respect to the i–th element of the light scattered by the particles of a unit particle quantity belonging to the particle diameter interval $[X_j, X_{j+1}]$.

The numeral value of $a_{i,j}$ can be theoretically calculated in advance. For this purpose, in case the particle diameter is sufficiently large when compared with a wavelength of the laser beam as a light source, the Fraunhofer's diffraction theory is used. However, in a submicron area where the particle diameter is the same size as the wavelength of the laser beam or smaller than that, the Mie's scattering theory must be used. The Fraunhofer's diffraction theory seems to extremely approximate to the Mie's scattering theory which is effective in case the particle diameter is sufficiently large when compared with the wavelength in the forward small angle scattering.

In order to calculate the elements of the coefficient matrix A based on the Mie's scattering theory, it is necessary to establish absolute refractive indices (complex numbers) of the particles and the medium (medium liquid) into which the particles are dispersed. Instead of the respective refractive indices, a relative refractive index (complex number) of the particles and the medium may be established.

Based on Equation (1), when a formula for obtaining the least square solution of the particle size distribution data (vector) q is found, Equation (5) can be obtained.

$$q = (A^T A)^{-1} A^T s \quad (5)$$

wherein $A^T$ is a transposed matrix of A, and $(\ )^{-1}$ is an inverse matrix.

The respective elements of the light intensity distribution data (vector) s in the right-hand side of Equation (5) are numeral values detected by the ring detector 24, forward large angle scattered light sensors 25, sideward scattered light sensors 26 and rearward scattered light sensors 27 as described before. Also, the coefficient matrix A can be obtained in advance by using the Fraunhofer's diffraction theory or Mie's scattering theory. Therefore, when calculation of Equation (5) is carried out by using these already known data, the particle size distribution data (vector) q can be obtained.

The above explanation is a basic measuring theory of the particle size distribution measurement based on the laser diffraction method. Incidentally, although only one example for calculating the particle size distribution has been shown, there are various other methods. Also, with respect to the optical system for measuring scattered light, there are many other variations. For example, a measuring optical system using an reverse Fourier optical system as shown in FIG. 3 has been known.

In the measuring optical system using the reverse Fourier optical system shown in FIG. 3, instead of irradiating the parallel laser beam to the particles to be measured as in the optical system shown in FIG. 2, the laser beam set to be parallel by a laser beam source 32a, condenser lens 32b, spatial filter 32c and collimator lens 32d are condensed by a condenser lens 32e positioned on the side of a flow cell 31, and then irradiated to a suspension S flowing in the flow cell 31. A ring detector 34 is disposed on a focal position of the condenser lens 32e. By using the reverse Fourier optical system, light scattered to a wide angle area can enter the ring detector 34. Incidentally, the forward large angle scattered light sensors 35, sideward scattered light sensors 36 and rearward scattered light sensors 37 are arranged in the same manner as shown in FIG. 2.

The ring detector 24 or 34 used in the conventional particle size analyzer based on the laser diffraction method is formed of a plurality of light receiving elements, wherein the light receiving surfaces are spatially continuously arranged without a space therebetween, so that light intensities for large scattering angle can be continuously measured. However, since the forward large angle scattered light sensors 25 or 35, sideward scattered light sensors 26 or 36 and rearward scattered light sensors 27 or 37 are separately disposed, the spatial intensity pattern of the scattered light can not be continuously measured.

The scattered light by particles having small diameters tends to have large scattering angle. Therefore, in order to measure a particle size distribution in an area containing the particles with small diameter in a high resolution, it is necessary to detect the scattered light having large scattering angle with a high resolution. Recently, it has been required to measure the particle size distribution in a submicron area with a higher resolution. In order to fulfill the requirement, as in the conventional measuring optical system as shown in FIG. 2, in case the measuring area of the light intensity distribution by the ring detector 24 is smaller than about 35°, it is impossible to improve the resolution in the submicron area more than that made at present.

On the other hand, according to the conventional measuring optical system using the reverse Fourier optical system as shown in FIG. 3, the light scattered to the larger angle when compared with the measuring optical system as shown in FIG. 2 can be measured by the ring detector 34. However, in the reverse Fourier optical system, since nonparallel laser beams are irradiated to the flow cell 31, it is not essentially expected to obtain a scatterered light pattern with a high resolution. More specifically, according to the reverse Fourier optical system, depending on the difference of the particle positions in the direction of an optical path length, even if the particles have the same diameter, entering positions thereof on the detecting surface of the ring detector 34 of the scattered light are different. Therefore, strictly speaking, only when the width, i.e. optical path length, of the flow cell 31 is zero, the measuring theory of the reverse Fourier optical system is established. However, actually, since it is also necessary to measure the particles with relatively large diameters, the optical path length in the flow cell 31 is required to be comparatively long. Thus, the measuring accuracy of an actual spatial intensity distribution is lowered, and the measurement can not be made with a high resolution.

In view of the above defects, the present invention has been made, and an object of the invention is to provide a particle size analyzer based on the laser diffraction method, wherein the parallel laser beam is irradiated to particles to be measured as in the conventional optical system and an optical path length in a flow cell has a practical length, but the measuring accuracy of a spatial intensity distribution of the scattered light is not lowered.

Another object of the invention is to provide a particle size analyzer based on the laser diffraction method, wherein the light scattered in a larger angle area can be measured with a high resolution, so that a resolution for the particle size distribution in a submicron area can be improved when compared with the conventional particle size analyzer.

Further objects and advantages of the invention will be apparent from the following description of the invention.

SUMMARY OF THE INVENTION

In order to attain the above objects, a particle size analyzer based on the laser diffraction method of the invention includes an irradiation optical system for irradiating parallel laser beam to particles to be measured in a dispersion state; a measuring optical system for measuring a spatial intensity distribution of the scattered light generated by the irradiation of the laser beam; and an operation or calculation device for calculating the particle size distribution of the particles by using the spatial intensity distribution of the scattered light. The measuring optical system includes a condenser lens for condensing the light scattered over a wide angle area from a forward small angle in the vicinity of 0° to over 40° and an optical sensor array for continuously detecting an intensity distribution of the light entering a detecting plane positioned at a focal point of the condenser lens. The calculation device first carries out correction operations of measuring errors of the scattered light intensity distribution caused by an aberration by the condenser lens and an attenuation on the optical path by comparing with the data obtained beforehand and stored through a ray tracing of the measuring optical system, and then calculates the particle size distribution.

The present invention uses the optical system, as shown in FIG. 2, wherein the parallel laser beam is irradiated to the particles to be measured, the forward scattered light by the particles to be measured is condensed by the condenser lens and a scattering image is formed on the optical sensor array capable of continuously measuring the spatial intensity distribution of light, represented by a ring detector. However, in the present invention, the area of the light condensed by the condenser lens and led to the optical sensor array are enlarged to an area from an angle in the vicinity of 0° to over 40°, and the attenuation and aberration of the light caused by condensing the light extending over such a wide angle area through the condenser lens are corrected by the calculation device based on the data obtained beforehand through the ray tracing, and then the particle size distribution can be calculated to thereby attain the expected objects.

In the optical system for irradiating the parallel laser beam to the particles to be measured as shown in FIG. 2, the reason why the range of light for forming an image on the ring detector by condensing the light through the condenser lens is in the order of less than 35° is that influences of the aberration by the condenser lens and attenuation of the light become noticeable in the measuring results of the spatial intensity distribution of the scattered light.

More specifically, an optical system is normally designed on the assumption that light with angle in a range for satisfying $\theta \approx \sin\theta \approx \tan\theta$ with respect to an optical axis is used. When the light exceeding the angle over the range, further, over 40°, are condensed by the condenser lens, an aberration of an image on a focal plane becomes large. Also, in case the light in larger angle passes through the lens or the like, reflection thereof becomes large, so that the intensity of the light is attenuated. Therefore, in case a right image is intended to be formed on the focal plane, the problem of this type is fatal. However, the purpose of a laser diffraction method is to detect the spatial intensity distribution pattern of the scattered light.

Thus, in order to attain the purpose, the aberration and attenuation caused when the light exceeding a wide angle area is condensed by the condenser lens to form an image are corrected according to the contents detected and stored beforehand through the ray tracing to thereby obtain an accurate spatial intensity distribution of the scattered light. Through calculation of the particle size distribution by using the data after the correction, an image of the scattered light exceeding the wide angle area is formed on the optical sensor array, such as a ring detector, capable of measuring the continuous spatial intensity distribution by using the condenser lens. Thus, the particle size distribution can be calculated based on the data measured with a high resolution, and the particle size distribution of the fine particles in a submicron area can be measured with a high resolution.

DETAILED DESCRIPTION OF PREFERRED EMBODIMENTS

Hereunder, an embodiment of the invention is explained with reference to the accompanying drawings.

Figure 1:
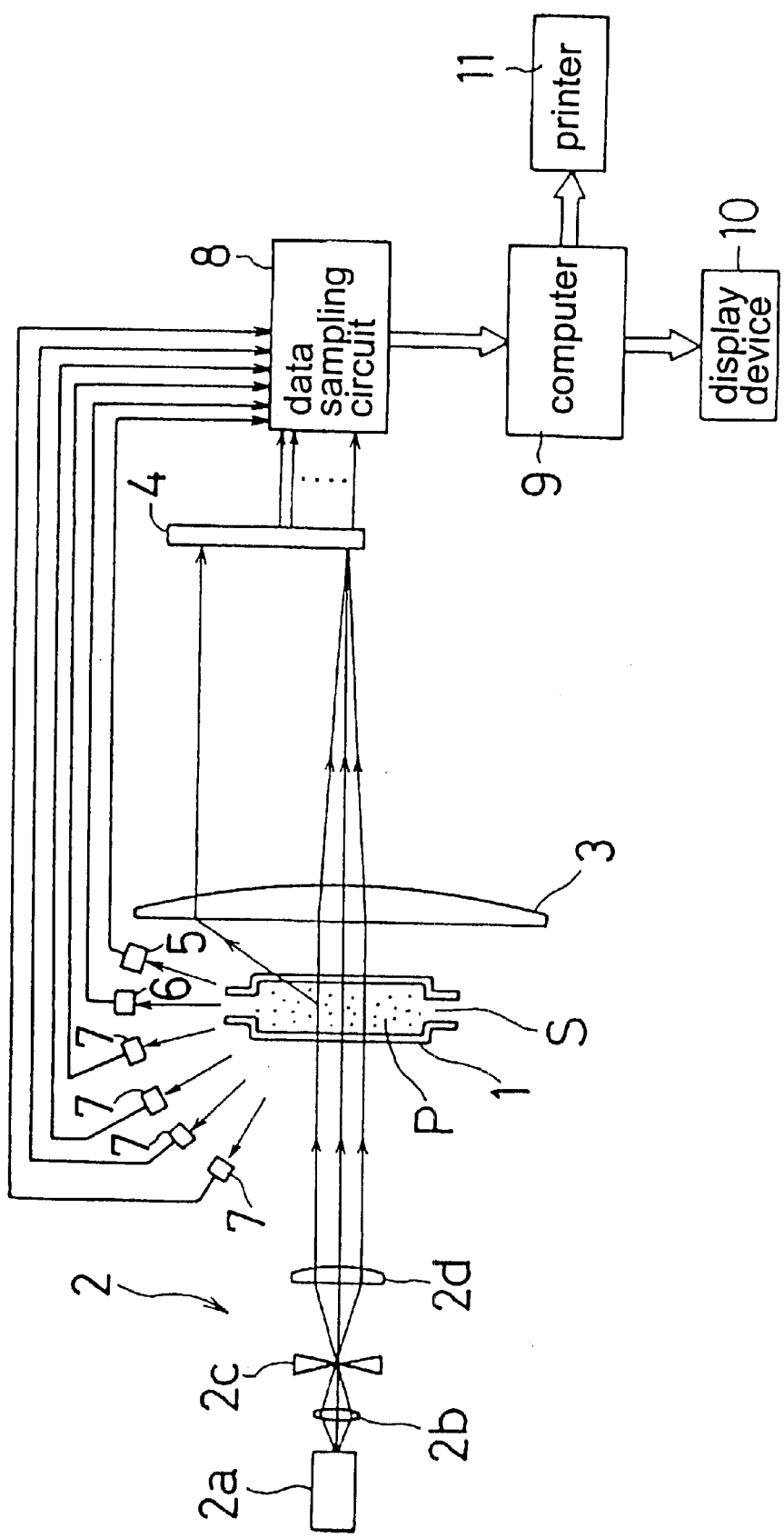
FIG. 1 is a diagram showing a structure of an embodiment according to the invention, wherein an optical system and an electrical structure are combined.
Figure 2:
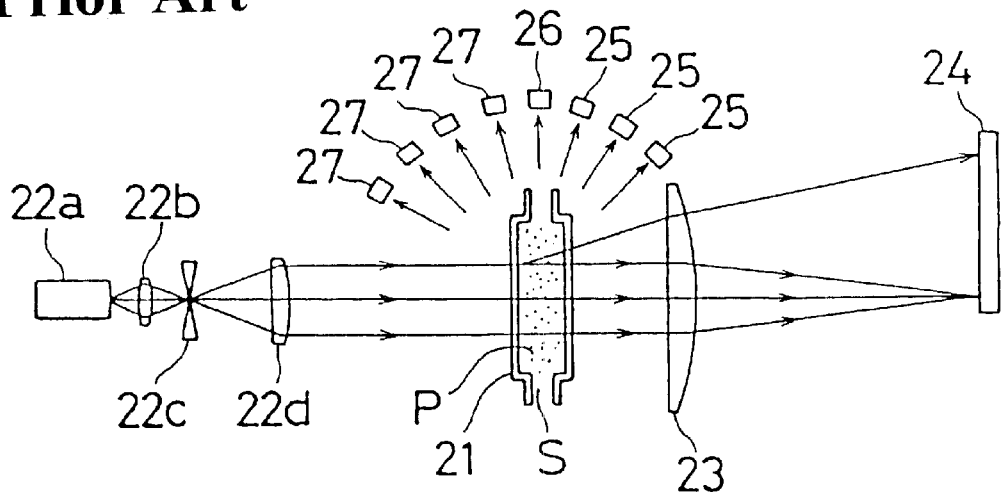
FIG. 2 is a diagram showing a structure of an optical system of a conventional particle size analyzer based on the laser diffraction method, wherein parallel laser beam is irradiated to particles to be measured, and obtained scattered light is condensed by a condenser lens and then led to a ring detector.
Figure 3:
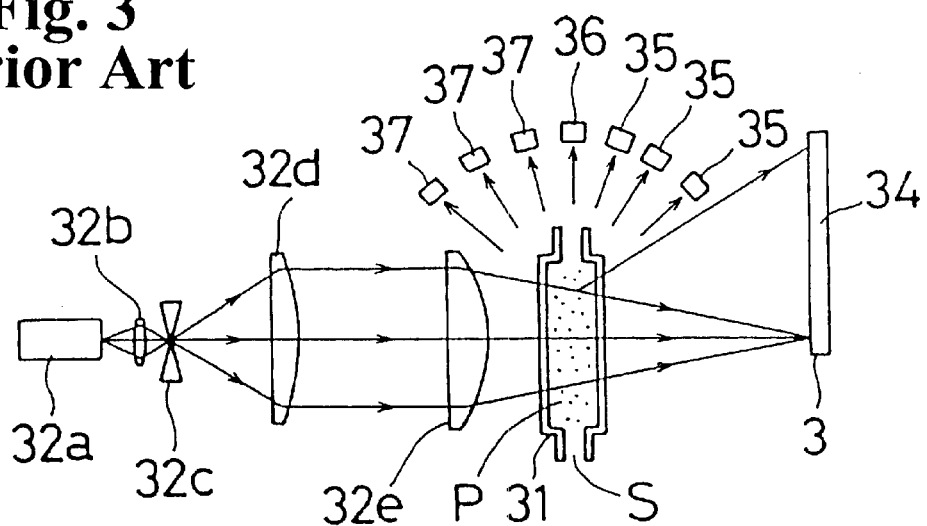
FIG. 3 is a diagram showing a structure of an optical system of a conventional particle size analyzer based on the laser diffraction method using an reverse Fourier optical system.

FIG. 1 is a diagram showing a structure of an embodiment of the invention, wherein an optical system and an electrical structure are combined.

A suspension S prepared by dispersing particles P to be measured in a medium liquid flows in a flow cell 1. Parallel laser beam is irradiated to the flow cell 1 from an irradiation optical system 2 formed of a laser beam source 2a, such as a semiconductor laser, a condenser lens 2b, a spatial filter 2c and a collimator lens 2d.

The scattered light by the respective particles caused when the parallel laser beam is irradiated to the particles P to be measured are condensed by a condenser lens 3 for covering a front angle area from the vicinity of 0° to over 40°, for example 60°, and a spatial intensity distribution of the light is detected by a ring detector 4 positioned at a focal position of the lens 3. Also, the scattered light having scattering angle larger than the angle area is detected by frontward large angle scattered light sensors 5, sideward scattered light sensors 6 and rearward scattered light sensors 7.

After outputs from the respective sensors are amplified and digitized at a data sampling circuit 8 formed of an amplifier and an A–D converter, they are taken into a computer 9 as scattered light intensity distribution data.

The computer 9 stores a program for carrying out a calculation based on Equation (5), described above, according to the Mie's scattering theory or the Fraunhofer's diffraction theory. Also, the computer 9 has a program for carrying out a correction of errors resulted from an aberration of the condenser lens 3 and attenuation on an optical path, in other words, attenuation caused mainly when the scattered light passes through the flow cell 1 and condenser lens 3 with respect to the scattered light data taken as described above. Then, the measured scattered light data are subjected to calculation of a particle size distribution after the correction is made. Incidentally, the measured results of the particle size distribution are displayed by a display device 10, or printed out by a printer 11.

The aberration by the condenser lens 3 and the attenuation of the scattered light on the optical path can be accurately measured theoretically by obtaining influences of the aberration and attenuation through accurate ray tracing in the passages where the light generated from particles pass through optical elements, such as the flow cell 1 and condenser lens 3, and medium, such as air, fluid or solid. Therefore, errors due to the aberration and attenuation of light passing through, especially, the large angle area out of the scattered light from the particles are obtained in advance through the ray tracing, and actually measured scattered light data are corrected, so that even scattered light to the large angle area covering to 60° beyond 40° can be measured with a high resolution by the ring detector 4 capable of measuring a continuous scattered light intensity distribution. Therefore, through calculation of a particle size distribution by using the corrected scattered light data, the particle size distribution in a submicron area can be measured with a high resolution.

Incidentally, in the above embodiment, the measured scattered light intensity distribution data are subjected to calculation of the particle size distribution after the errors obtained and stored in advance through the ray tracing are corrected. However, by incorporating information relating to the aberration and attenuation obtained from the ray tracing into the respective elements $a_{i,j}$ of coefficient matrix A for converting the intensity distribution data of the scattered light to the particle size distribution data in advance, an calculation based on Equation (5) may of course be carried out to obtain the particle size distribution by using the measured scattered light intensity distribution data as they are.

Also, in the above embodiment, the light condensed by the condenser lens 3 is measured by the ring detector 4 positioned at a focal point of the lens 3. However, the present invention is not limited to the ring detector as the optical sensor array for detecting light condensed by the condenser lens 3. It is possible to employ any other arrays wherein an intensity distribution of scattered light can be continuously measured, such as, an optical sensor array wherein a plurality of light receiving elements, each having a rectangular light receiving surface, is closely and linearly arranged.

Also, in the above embodiment, the present invention is applied to a wet type measuring apparatus wherein the laser beam is irradiated to the suspension S in which the particles P to be measured are dispersed in the medium liquid. However, of course, the present invention can also be applied to a dry type measuring apparatus wherein the particles P to be measured are set in an aerosol state to which the laser beam is irradiated.

As described above, according to the present invention, since scattered light covering a wide angle area from an angle in the vicinity of 0° to over 40° are condensed by the condenser lens; the intensity distribution of the scattered light is continuously measured by the optical sensor array, such as the ring detector, the detecting surface of which is positioned at the focal position; and the measured results of the scattered light are subjected to calculation of the particle size distribution after the errors due to the aberration and attenuation obtained through the ray tracing are corrected. Thus, it is possible to accurately measure the scattered light covering the large angle area with a high resolution to thereby obtain a particle distribution in the submicron area with a higher resolution when compared with the conventional particle size analyzer.

As a result, for example, in case a sample prepared by mixing two kinds of powders is measured, when its resolution is low, the measured results show that the sample has a wide distribution with one peak. However, in case its resolution is high as in the present invention, peaks of the respective powders can be measured.

Also, in case two samples having very close particle diameters, i.e. average particle diameters, are measured, when the resolution is low, differences between the two samples are not observed. However, when the resolution is high as in the present invention, the difference between the two samples becomes apparent.

Further, in case two samples having the same average particle diameter and distributed in different distribution areas are measured, when the resolution is low, measured results of a wider distribution area can be obtained for both samples. However, when the resolution is high as in the present invention, the difference between the sample having a narrow distribution area and the sample having a wide distribution area becomes apparent.

While the invention has been explained with reference to the specific embodiments of the invention, the explanation is illustrative and the invention is limited only by the appended claims.

What is claimed is:

1. A particle size analyzer, comprising:

an irradiation optical system for irradiating parallel laser beam to particles to be measured in a dispersion state;

a measuring optical system for measuring a spatial intensity distribution of scattered light generated by irradiation of the laser beam, said measuring optical system including a condenser lens for condensing the scattered light scattered over a wide angle area, and an optical sensor for continuously detecting an intensity distribution of lights entering a detecting surface thereof positioned at a focal point of the condenser lens; and a calculation device for calculating a particle size distribution of the particles to be measured by using the spatial intensity distribution of the scattered light by the optical sensor, said calculation device having correction means for carrying out a correction operation of measuring an error of the scattered light intensity distribution caused by an aberration by the condenser lens and an attenuation in an optical path by comparing data obtained and stored in advance through a ray tracing of the measuring optical system with a value obtained at the optical sensor, said calculation device calculating the particle size distribution after the correction operations.

2. A particle size analyzer according to claim 1, wherein said condenser lens condenses the light scattered over an angle area from a forward angle of 0° to about 60°.

3. A particle size analyzer according to claim 2, wherein said measuring optical system further includes front large angle scattered light sensors situated adjacent to the optical sensor, side scattered light sensors situated at side portions of the sample to be measured and rear scattered light sensors situated at rearward of the sample.

4. A particle size analyzer according to claim 3, further comprising a data sampling circuit electrical connected to the optical sensor and all the light sensors.

* * * * *